(12) United States Patent
Sasaki

(10) Patent No.: US 7,495,095 B2
(45) Date of Patent: Feb. 24, 2009

(54) THIONUCLEOSIDE-S-NITROSYL DERIVATIVE

(75) Inventor: Shigeki Sasaki, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 351 days.

(21) Appl. No.: 10/554,158

(22) PCT Filed: Mar. 12, 2004

(86) PCT No.: PCT/JP2004/003337

§ 371 (c)(1),
(2), (4) Date: Dec. 8, 2005

(87) PCT Pub. No.: WO2004/094447

PCT Pub. Date: Nov. 4, 2004

(65) Prior Publication Data

US 2006/0199953 A1    Sep. 7, 2006

(30) Foreign Application Priority Data

Apr. 22, 2003   (JP) ............................. 2003-117569

(51) Int. Cl.
*C07H 19/167*  (2006.01)
*C07H 19/173*  (2006.01)

(52) U.S. Cl. .................. 536/27.8; 536/25.3; 536/27.1; 536/27.13; 536/27.2; 536/27.21

(58) Field of Classification Search ........................ None
See application file for complete search history.

(56) References Cited

FOREIGN PATENT DOCUMENTS

JP    2000-506492 A    5/2000

OTHER PUBLICATIONS

International Search Report for PCT/JP2004/003337 mailed May 25, 2004.
Amado et al, "Kinetics and mechanism of the formation and reactions of S-nitroso derivatives of some heterocyclic thiones", Journal of the Chemical Society, Perkin Transactions 2, 2001, No. 4, pp. 441-447.

*Primary Examiner*—Patrick T Lewis
(74) *Attorney, Agent, or Firm*—Darby & Darby P.C.

(57) ABSTRACT

The present invention provides a thionucleoside-S-nitrosyl derivative of the following Formula I or a salt thereof:

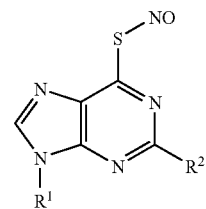

[wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group (wherein $R^3$ represents an optionally substituted $C_{1-15}$ alkyl group or an optionally substituted $C_{1-15}$ acyl group)].

10 Claims, 13 Drawing Sheets

Hydrolysis of N-nitroso form into carbonyl group

THIONUCLEOSIDE-S-NITROSYL DERIVATIVE

CROSS-REFERENCE TO PRIOR APPLICATION

This is a U.S. National Phase application under 35 U.S.C. §371 of International Patent Application No. PCT/JP2004/003337 filed Mar. 12, 2004, and claims the benefit of Japanese Patent Application No. 2003-117569 filed Apr. 22, 2003, both of which are incorporated by reference herein. The International Application was published in Japanese on Nov. 4, 2004 as WO 2004/094447 A1 under PCT Article 21(2).

TECHNICAL FIELD

The present invention pertains to the technical field of manipulating nucleic acids, and more particularly relates to a thionucleoside-S-nitrosyl derivative which is a novel compound useful in obtaining an oligonucleic acid capable of recognizing a specific base and transferring a nitrosyl group in a sequence-specific manner.

BACKGROUND ART

A method is known for regulating gene expression by establishing a specific binding between a nucleic acid of a specific gene and an oligonucleic acid or nucleic acid analog specific to the nucleic acid sequence of the gene to form a chemical bond (see, e.g., "Genome Chemistry," edited by Sekine/Saitoh, Kodansha Ltd., 2003, Tokyo, Japan). In particular, recent studies have shown that depending on the structure of a chemical bond, a point mutation can be induced at the binding site (see, e.g., Nagatsugi, F., Sasaki, S., Miller, P. S., Seidman, M. M., Nucl. Acid Res, Vol. 31(6), e31 (2003)). Such a method for inducing point mutations in a sequence-specific manner is not only used as a biochemical experimental tool, but also has the possibility of being applicable to radical treatment of various diseases including gene abnormalities, thus receiving great attention in the fields of biochemistry, medicine and pharmacy.

On the other hand, nitric oxide (NO) plays an important role as an intracellular signal transmitter (see, e.g., L. J. Ignarro, Pharmacology & Toxicology, 67(1), 1, (1990)). In the body, S-nitrosothiol is believed to serve as a nitric oxide (NO) carrier (see, e.g., D. L. H. Wiliams, Acc. Chem. Res., 32, 869 (1999)). In addition to its role in signal transduction, nitric oxide (NO) also serves as an oxidizing agent in vivo to react with bases in DNA or RNA. It is therefore believed that NO may be responsible for point mutations. Moreover, chemical experiments have been found to cause non-specific mutations (see, e.g., J. L. Caulfield, J. S. Wishnok, S. R. Tannenbaum, J. Biol. Chem. 273(21), 12689 (1998); N. Y. Tretyakova, S. Burney, B. Pamir, J. S. Wishnok, P. C. Dedon, G N. Wogan, S. R. Tannenbaum, Mutation Research 447(2), 287 (2000)).

Recently, a report has been published on a method for DNA repair by DNA strand exchange, in which modified oligonucleotides are used to create a mismatch-containing double insert (M. D. Drury, E. B. Kmiec, Nucleic Acids Research 31(3), 899 (2003)). However, this method, which uses a model experimental system, provides low repair efficiency and also has many problems to be solved before being adapted for use in cellular systems.

DISCLOSURE OF THE INVENTION

The object of the present invention is to provide a thionucleoside-S-nitrosyl derivative, an oligonucleic acid capable of specifically transferring a nitrosyl group to a target nucleic acid, and a method for sequence-specific mutagenesis.

As a result of extensive and intensive efforts made to overcome the problems stated above, the inventors of the present invention have succeeded in synthesizing an oligonucleotide containing a novel nitrosyl compound through nitrosylation using an oligonucleotide modified to have a structure in which a carbonyl group in the skeletal structure of natural nucleobases is converted into a thiocarbonyl group. Moreover, the inventors have also found that this oligonucleotide transfers a nitrosyl group in a sequence-specific and base-specific manner. This finding led to the completion of the present invention.

Namely, the present invention is as follows.

(1) A thionucleoside-S-nitrosyl derivative of the following Formula (I) or a salt thereof:

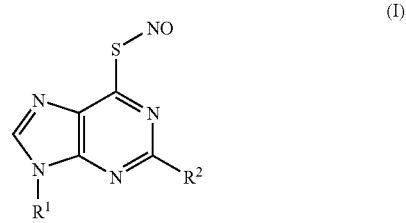

[wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group (wherein $R^3$ represents an optionally substituted $C_{1-15}$ alkyl group or an optionally substituted $C_{1-15}$ acyl group)].

(2) A thionucleoside-S-nitrosyl derivative of the following Formula (II) or a salt thereof:

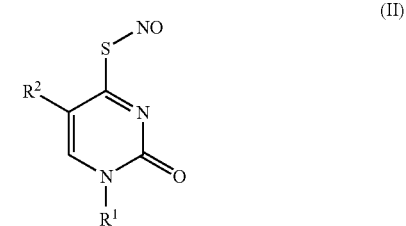

[wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group (wherein $R^3$ represents an optionally substituted $C_{1-15}$ alkyl group or an optionally substituted $C_{1-15}$ acyl group)].

(3) A thionucleoside-S-nitrosyl derivative of the following Formula (III) or a salt thereof:

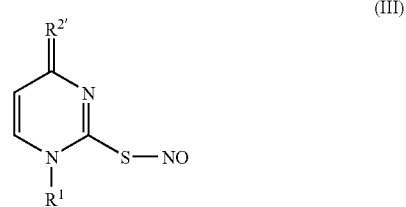

(wherein R¹ represents ribose, 2-deoxyribose or a derivative of either, and R²' represents an oxygen atom, a sulfur atom or an imino group).

(4) A method for preparing a thionucleoside-S-nitrosyl derivative, which comprises reacting a thionucleoside of the following Formula (IV):

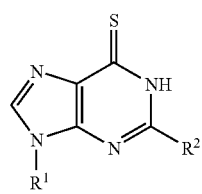

(IV)

[wherein R¹ represents ribose, 2-deoxyribose or a derivative of either, and R² represents a hydrogen atom, an amino group, a hydroxyl group, a halogen atom, a R³-oxy group or a R³-amino group (wherein R³ represents an optionally substituted $C_{1-15}$ alkyl group or an optionally substituted $C_{1-15}$ acyl group)] with an S-nitrosyl compound.

(5) A method for preparing a thionucleoside-S-nitrosyl derivative, which comprises reacting a thionucleoside of the following Formula (V):

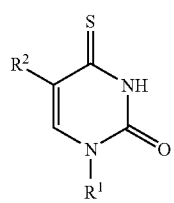

(V)

[wherein R¹ represents ribose, 2-deoxyribose or a derivative of either, and R² represents a hydrogen atom, an amino group, a hydroxyl group, a halogen atom, a R³-oxy group or a R³-amino group (wherein R³ represents an optionally substituted $C_{1-15}$ alkyl group or an optionally substituted $C_{1-15}$ acyl group)] with an S-nitrosyl compound.

(6) A method for preparing a thionucleoside-S-nitrosyl derivative, which comprises reacting a thionucleoside of the following Formula (VI):

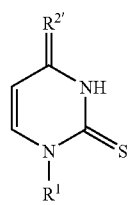

(VI)

[wherein R¹ represents ribose, 2-deoxyribose or a derivative of either, and R²' represents an oxygen atom, a sulfur atom or an imino group] with an S-nitrosyl compound.

(7) An oligonucleic acid comprising the derivative according to any one of (1) to (3) above or a salt thereof.

Examples of the oligonucleic acid of the present invention include, for example, those having a length of at least 12 bases.

(8) A method for transferring a nitrosyl group, which comprises reacting the oligonucleic acid according to (7) above with a complementary strand corresponding to the oligonucleic acid to transfer the nitrosyl group contained in said oligonucleic acid to its corresponding base.

(9) A method for mutagenesis of a nucleotide sequence, which comprises reacting the oligonucleic acid according to (7) above with its complementary strand, and treating the resulting reaction product under acidic conditions.

According to the mutagenesis method of the present invention, when the nitrosyl group contained in the above oligonucleic acid is transferred to a corresponding base in its complementary strand, the corresponding base can be mutated to uracil in the reaction product between the oligonucleic acid and its complementary strand.

(10) A mutagenic agent for a nucleotide sequence or a mutagenesis kit for a nucleotide sequence, which comprises at least one member selected from the group consisting of the derivative according to any one of (1) to (3) above and the oligonucleic acid according to (7) above.

BEST MODE FOR CARRYING OUT THE INVENTION

Figure 1:
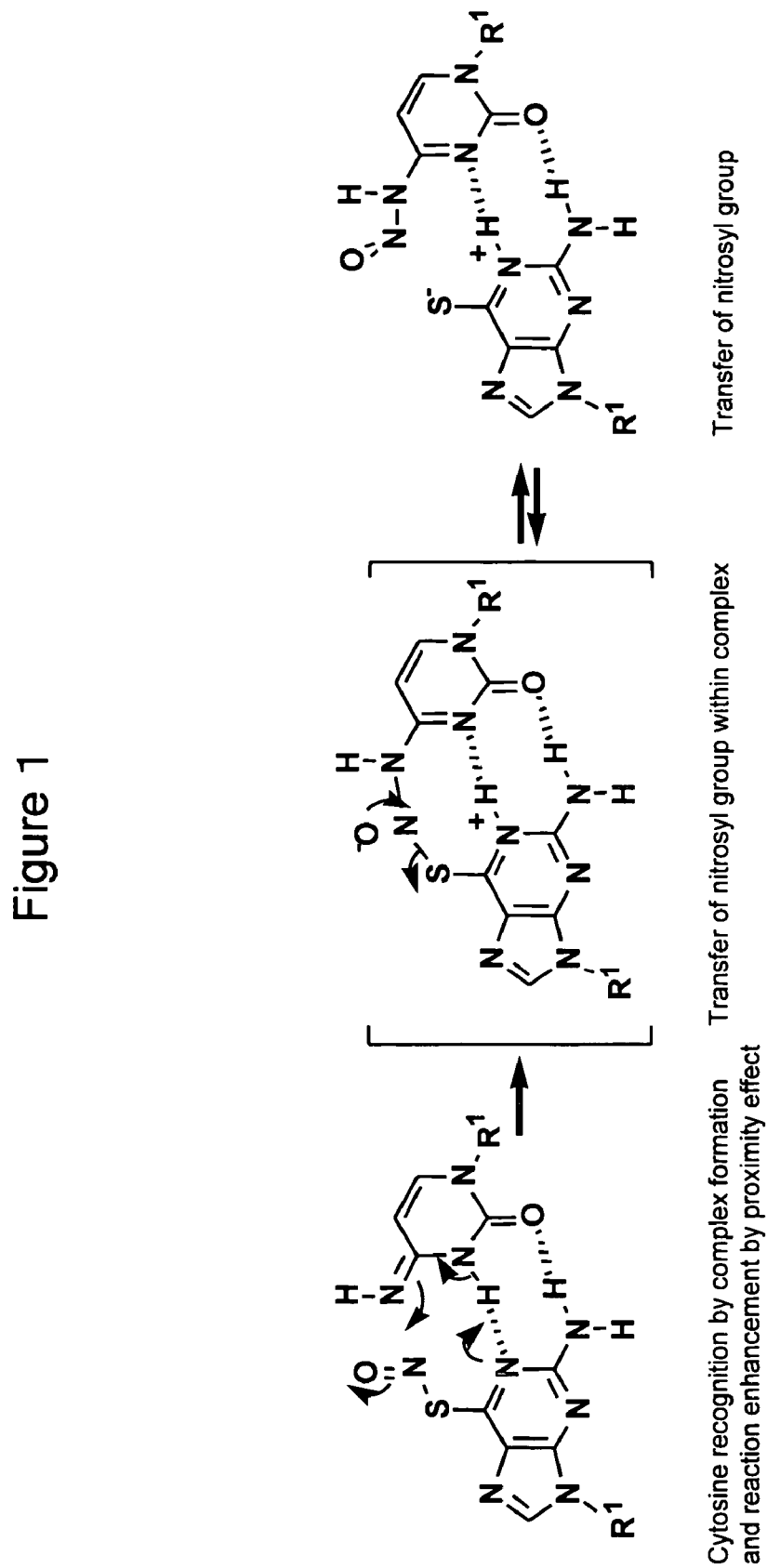
FIG. 1 shows nitrosyl group transfer achieved by the derivative of the present invention.

The present invention will be described in more detail below.

The derivative of the present invention is characterized by having a structure in which a nitrosyl group is attached onto the sulfur atom of a thionucleoside. The derivative of the present invention is also characterized in that it recognizes and binds to a specific base to thereby transfer its own nitrosyl group to the base in its binding partner.

1. Thionucleoside-S-nitrosyl derivatives

In the compound of the present invention (i.e., a thionucleotide-S-nitrosyl derivative) represented by the above Formula (I), (II) or (III), $R^1$ represents ribose, 2-deoxyribose or a derivative of either. $R^2$ represents a hydrogen atom, an amino group, a hydroxyl group, a halogen atom, a $R^3$-oxy group or a $R^3$-amino group. $R^{2'}$ represents an oxygen atom, a sulfur atom or an imino group.

$R^3$ represents an optionally substituted $C_{1-15}$ alkyl group or an optionally substituted $C_{1-15}$ acyl group. Such an alkyl or acyl group preferably contains 1 to 10 carbon atoms, and more preferably 1 to 5 carbon atoms.

The alkyl group may be linear, branched or cyclic and examples include a methyl group, an ethyl group, a n-propyl group, an isopropyl group, a n-butyl group, a t-butyl group, a n-pentyl group, a n-hexyl group, a cyclohexyl group, a n-heptyl group, a n-octyl group, and a n-dodecyl group.

The $C_{1-15}$ acyl group refers to an optionally substituted linear or branched alkylacyl group, an optionally substituted cycloalkylcarbonyl group, or an optionally substituted benzoyl group, etc.

Examples of an alkylacyl group include a formyl group, an acetyl group, a propionyl group, a n-butyryl group, an isobutyryl group, a 2-methylbutyryl group, a 3-methylbutyryl group, a pivaloyl group, a valeryl group, a 2-methylvaleryl group, a caproyl group, a heptanoyl group, an octanoyl group, and a decanoyl group.

Examples of a cycloalkylcarbonyl group include a cyclopropanecarbonyl group, a cyclohexanecarbonyl group, and a cyclopentanecarbonyl group.

In an optionally substituted benzoyl group, its phenyl group may be unsubstituted or substituted at any of the 2-, 3- and 4-positions. Alternatively, the phenyl group may also have substituents at multiple positions. In this case, these substituents may be the same or different.

Examples of a substituent on the phenyl group include an alkyl group (e.g., a methyl group, an ethyl group, an isopropyl group); an alkyloxy group (e.g., a methoxy group, an ethoxy group, a n-propyloxy group); a substituted or unsubstituted amino group (e.g., a nitro group, an amino group, a methylamino group, an ethylamino group, a n-propylamino group, an i-propylamino group, a dimethylamino group, a diethylamino group); a halogen group (e.g., a fluoro group, a chloro group, a bromo group); an acyl group (e.g., a formyl group, an acetyl group, a propionyl group, a benzoyl group); an acyloxy group (e.g., a formyloxy group, an acetyloxy group, a propionyloxy group, a benzoyloxy group); an amido group (e.g., a formamido group, an acetamido group, a benzamido group); and an aromatic ring (e.g., a phenyl group).

Specific examples of an optionally substituted benzoyl group include a benzoyl group, a 2-methoxybenzoyl group, a 3-methoxybenzoyl group, a 4-methoxybenzoyl group, a 2-methylbenzoyl group, a 3-methylbenzoyl group, a 4-methylbenzoyl group, a 2-nitrobenzoyl group, a 3-nitrobenzoyl group, a 4-nitrobenzoyl group, a 3,5-dinitrobenzoyl group, a 2-aminobenzoyl group, a 3-aminobenzoyl group, a 4-aminobenzoyl group, a 4-dimethylaminobenzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 3,5-dichlorobenzoyl group, a 2,4-dichlorobenzoyl group, a perchlorobenzoyl group, and a 4-phenylbenzoyl group.

Ribose or deoxyribose is represented by the following Formula (VII):

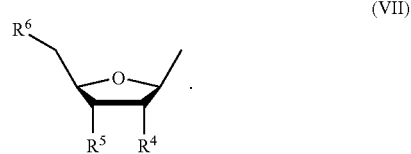

(VII)

In Formula (VII), $R^4$ represents a hydroxyl group (for ribose) or a hydrogen atom (for deoxyribose). $R^5$ and $R^6$, which may be the same or different, each independently represent, e.g., a hydrogen atom, a halogen group or an optionally substituted hydroxyl group, regardless of whether Formula (VII) represents ribose or deoxyribose or a derivative of either.

The halogen group defined for $R^5$ and/or $R^6$ refers to a fluorine atom, a chlorine atom, a bromine atom or an iodine atom. Likewise, the substituted hydroxyl group defined for $R^4$ and/or $R^5$ refers to a hydroxyl group which is substituted with a substituent capable of serving as a standard protecting group for a hydroxyl group (e.g., carboxylic acid ester, sulfonic acid ester, ether, urethane and silyl groups).

Examples of a protecting group for a hydroxyl group include an alkyl group (e.g., a methyl group, an ethyl group, a n-propyl group, an isopropyl group, a n-butyl group, an i-butyl group, a t-butyl group, a pentyl group, a benzyl group, a 2-methoxybenzyl group, a 3-methoxybenzyl group, a 4-methoxybenzyl group, a 2-methylbenzyl group, a 3-methylbenzyl group, a 4-methylbenzyl group, a methoxyethyl group, an ethoxyethyl group, a benzyloxymethyl group, a benzyloxyethyl group, an acetoxymethyl group, an acetoxyethyl group, a benzoyloxymethyl group, a benzoyloxyethyl group); an aryl group (e.g., a phenyl group, a 2-methoxyphenyl group, a 3-methoxyphenyl group, a 4-methoxyphenyl group, a 4-phenylphenyl group, a 2-pyridinyl group, a 3-pyridinyl group, a 4-pyridinyl group); an acyl group (e.g., a formyl group, an acetyl group, a propionyl group, a benzoyl group, a 2-methoxybenzoyl group, a 3-methoxybenzoyl group, a 4-methoxybenzoyl group, a 2-methylbenzoyl group, a 3-methylbenzoyl group, a 4-methylbenzoyl group, a 2-nitrobenzoyl group, a 3-nitrobenzoyl group, a 4-nitrobenzoyl group, a 4-phenylbenzoyl group); a urethane group (e.g., an aminocarbonyl group, a dimethylaminocarbonyl group, a methylaminocarbonyl group, an ethylaminocarbonyl group, a diethylaminocarbonyl group, a phenylaminocarbonyl group); a sulfonic acid ester group (e.g., a methanesulfonyl group, an ethanesulfonyl group, a benzenesulfonyl group, a 2-methylbenzenesulfonyl group, a 3-methylbenzenesulfonyl group, a 4-methylbenzenesulfonyl group, a trifluoromethanesulfonyl group, a trichloromethanesulfonyl group); and a silyl group (e.g., a trimethylsilyl group, a triethylsilyl group, a t-butyldimethylsilyl group, a t-butyldiphenylsilyl group).

Among compounds of Formula (I) according to the present invention, preferred are those wherein $R^1$ is deoxyribose and $R^2$ is an amino group. More preferred are those wherein $R^1$ is a 3',5'-bis-t-butyldimethylsilyl derivative of ribose or deoxyribose, and $R^2$ is an amino group.

Among compounds of Formula (II) according to the present invention, preferred are those wherein $R^1$ is deoxyribose and $R^2$ is an amino group. More preferred are those wherein $R^1$ is a 3',5'-bis-t-butyldimethylsilyl derivative of ribose or deoxyribose, and $R^2$ is an amino group.

Among compounds of Formula (III) according to the present invention, preferred are those wherein $R^1$ is deoxyribose and $R^{2'}$ is an oxygen atom or an imino group. More preferred are those wherein $R^1$ is a 3',5'-bis-t-butyldimethylsilyl derivative of ribose or deoxyribose, and $R^{2'}$ is an oxygen atom or an imino group.

2. Preparation of the Compounds of the Present Invention

Compounds of Formula (I), (II) or (III) according to the present invention can be synthesized by modification of known reactions.

(1) Preparation of Compounds of Formula (I)

In the present invention, to prepare a compound of Formula (I), a thionucleoside compound of the following Formula (IV):

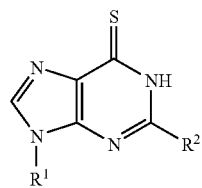

(IV)

(wherein $R^1$ and $R^2$ are as defined above) is reacted with a nitrosyl compound. An example of the reaction will be given below.

Namely, in a case where the compound of Formula (IV) is water-soluble, this compound is dissolved in carbonate buffer (pH 10) to prepare a solution of about 0.5 mM concentration. To this solution, a nitrosylating reagent (about 1 mM) is added and reacted at room temperature for 12 hours. The reaction solution is purified by HPLC (ODS column, solvent: 0.1 M triethylamine acetate-acetonitrile: linear gradient from 10% to 30%, detected at 254 nm) to obtain the S-nitrosyl form of interest. In a case where the compound of Formula (IV) is poorly water-soluble, this compound is dissolved in an organic solvent (e.g., acetonitrile or methanol) and triethylamine is added thereto in an amount of 10 equivalents of the starting material, followed by reacting them. Examples of a nitrosylating reagent include S-nitroso-N-acetylpenicillamine, nitric oxide and the like.

In the case of using sodium nitrite for the reaction, the compound of Formula (IV) is dissolved in an acidic buffer (pH 3) and sodium nitrite is used in an amount of about 10 equivalents.

(2) Preparation of Compounds of Formula (II)

Likewise, to prepare a compound of Formula (II), a thionucleoside of the following Formula (V):

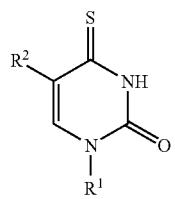

(V)

(wherein $R^1$ and $R^2$ are as defined above) is reacted with a nitrosyl compound. An example of the reaction will be given below.

Namely, in a case where the compound of Formula (V) is water-soluble, this compound is dissolved in carbonate buffer (pH 10) to prepare a solution of about 0.5 mM concentration. To this solution, a nitrosylating reagent (about 1 mM) is added and reacted at room temperature for 12 hours. The reaction solution is purified by HPLC (ODS column, solvent: 0.1 M triethylamine acetate-acetonitrile: linear gradient from 10% to 30%, detected at 254 nm) to obtain the S-nitrosyl form of interest. In a case where the compound of Formula (IV) is poorly water-soluble, this compound is dissolved in an organic solvent (e.g., acetonitrile or methanol) and triethylamine is added thereto in an amount of 10 equivalents of the starting material, followed by reacting them. Examples of a nitrosylating reagent include S-nitroso-N-acetylpenicillamine, nitric oxide and the like.

In the case of using sodium nitrite for the reaction, the compound of Formula (V) is dissolved in an acidic buffer (pH 3) and sodium nitrite is used in an amount of about 10 equivalents.

(3) Preparation of Compounds of Formula (III)

To prepare a compound of Formula (III), a thionucleoside of the following Formula (VI):

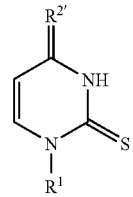

(VI)

(wherein $R^1$ and $R^{2'}$ are as defined above) is reacted with a nitrosyl compound. An example of the reaction will be given below.

Namely, in a case where the compound of Formula (VI) is water-soluble, this compound is dissolved in carbonate buffer (pH 10) to prepare a solution of about 0.5 mM concentration. To this solution, a nitrosylating reagent (about 1 mM) is added and reacted at room temperature for 12 hours. The reaction solution is purified by HPLC (ODS column, solvent: 0.1 M triethylamine acetate-acetonitrile: linear gradient from 10% to 30%, detected at 254 nm) to obtain the S-nitrosyl form of interest. In a case where the compound of Formula (IV) is poorly water-soluble, this compound is dissolved in an organic solvent (e.g., acetonitrile or methanol) and triethylamine is added thereto in an amount of 10 equivalents of the starting material, followed by reacting them. Examples of a nitrosylating reagent include S-nitroso-N-acetylpenicillamine, nitric oxide and the like.

In the case of using sodium nitrite for the reaction, the compound of Formula (VI) is dissolved in an acidic buffer (pH 3) and sodium nitrite is used in an amount of about 10 equivalents.

(4) Salts of the Compounds of the Present Invention

The above compounds of Formula (I), (II) or (III) according to the present invention may form acid addition salts or base addition salts. These salts also fall within the scope of the present invention. In a case where the compound of the present invention is used as an oligonucleic acid that is applicable in vivo or as an intermediate for its preparation, physiologically acceptable salts are preferred for this purpose. Examples of base addition salts include salts with amines such as triethylamine, dimethylamine, ammonia and diethylamine, as well as salts with metals such as sodium, potassium, calcium and magnesium. Examples of acid adducts include salts with mineral acids such as hydrochloric acid, sulfuric acid and perchloric acid, as well as salts with organic acids such as oxalic acid, fumaric acid, maleic acid, acetic acid, propionic acid, methanesulfonic acid and p-toluenesulfonic acid.

3. Oligonucleic Acids

Since the compound of Formula (I), (II) or (III) according to the present invention is a nucleoside, this compound can be converted into a nucleotide and used as a member constituting nucleic acids when attached to phosphoric acid via an ester linkage.

The nucleotide thus obtained may be incorporated into an appropriate oligonucleic acid and used as an oligonucleic acid capable of transferring a nitrosyl group in a sequence-specific manner. The phrase "transferring a nitrosyl group" means that the nitrosyl group in the oligonucleic acid of the present invention (i.e., the nitrosyl group present in the compound of the present invention) is transferred to a base in a nucleic acid partner that reacts with the oligonucleic acid to form a duplex (complex) (said base being also referred to as a target base) (FIG. 1).

The oligonucleic acid of the present invention may have any sequence and may be designed according to the sequence of a nucleic acid used as a template or may be designed to have a random nucleotide sequence. In a case where nitrosyl groups are attempted to be transferred to the nucleotide sequence of a certain gene, the oligonucleic acid may be designed to be complementary to a target nucleotide sequence of the gene (in this case, when viewing from the oligonucleic acid of the present invention, the nucleotide sequence of the gene is a complementary strand of the oligonucleic acid). In a case where the oligonucleic acid of the present invention is designed to have a random nucleotide sequence, nitrosyl groups are introduced into any base in the sequence. It is therefore possible to synthesize a nucleic acid having a sequence complementary to the above random nucleotide sequence, such that these nitrosyl groups are to be transferred (in this case, when viewing from the oligonucleic acid of the present invention, the synthesized nucleic acid is a complementary strand of the oligonucleic acid).

Figure 5:
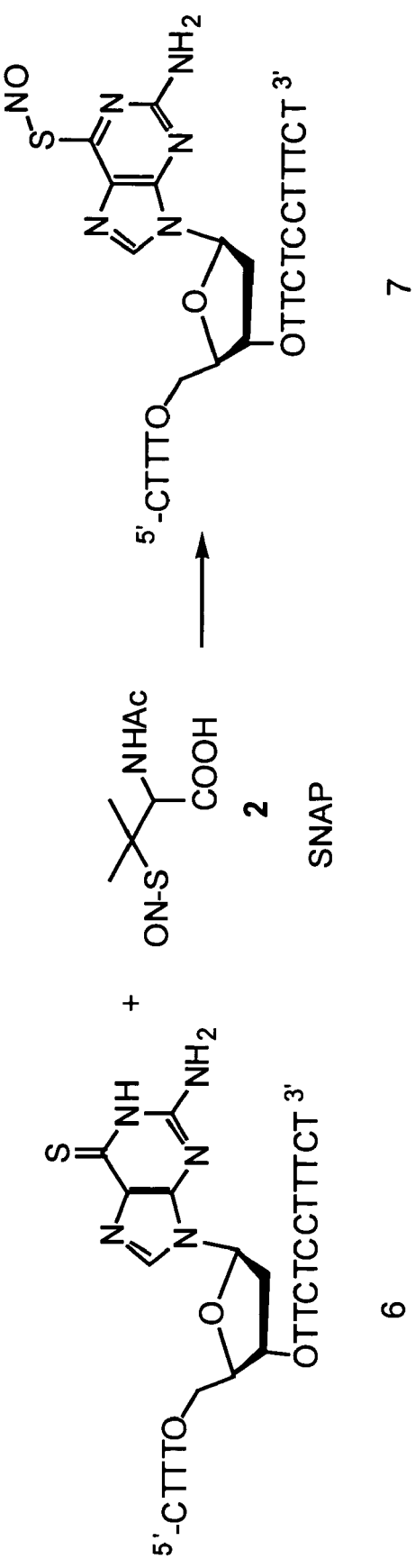
FIG. 5 shows a synthesis process for the nitrosylated oligonucleic acid of the present invention.

The oligonucleic acid sequence of the present invention may have any length as long as the nitrosyl group in the compound of the present invention can be transferred to its target base. In the present invention, the oligonucleic acid sequence preferably has at least 12 bases, and more preferably 15 to 22 bases. Although the compound of the present invention may be incorporated at any position in the oligonucleic acid, particularly in the case of developing sequence specificity, the compound of the present invention may preferably be incorporated within a region between the third bases from both ends of the oligonucleic acid. For example, as shown in FIG. 5, Oligonucleic acid 7 according to the present invention has 16 bases, in which the compound of the present invention is located at the fifth position. Moreover, the number of the compounds of the present invention contained in the oligonucleic acid of the present invention is not necessarily limited to only one. The compound of the present invention may also be incorporated at multiple positions. Namely, in the oligonucleic acid of the present invention, there is no particular limitation on the number of target bases into which nitrosyl groups are introduced. In a case where the derivative is located at multiple positions, two or more derivatives may be adjacent to each other or located at discrete positions.

The oligonucleic acid may be synthesized in a known manner using commercially available reagents and synthesizer for nucleic acid synthesis. An example will be given below of the synthesis using a compound of Formula (IV) [wherein $R^1$ is 2-deoxyribose]. A 5'-O-p-dimethoxytrityl-3'-O-(β-cyanoethyl-diisopropylphosphoroamidite) form of Formula (IV) (about 80 mmol) is dissolved in anhydrous acetonitrile and charged into an automatic DNA synthesizer (Applied Biosystems 394 DNA/RNA Synthesizer). According to a standard program stored in the synthesizer, the synthesis is performed using a 1 μmol column and, after completion of the synthesis, the product is excised from the solid phase column in 28% aqueous ammonia, warmed at 55° C. for 5 hours to effect base deprotection, and then purified by HPLC connected to an ODS column (ODS column, acetonitrile-0.1 M TEAA=10%-40% linear gradient/20 minutes). Further, deprotection of the p-dimethoxytrityl group and purification are performed using a porous column (50 mM ammonium acetate, pH 10→5% acetonitrile-50 mM ammonium acetate→2% trifluoroacetic acid→50 mM ammonium acetate→65% methanol). Purity assay and structure confirmation may be accomplished, for example, by molecular weight determination using MALDI-TOF MS (Perseptive Biosystems, Voyager Elite, 3-hydroxy-2-picolinic acid-diammonium hydrogen citrate matrix).

4. Nitrosyl Group Transfer Reaction

The mechanism by which the compound of Formula (I), (II) or (III) transfers its nitrosyl group is achieved in a complex structure formed by complementary hydrogen bonding, as shown in FIG. 1. It should be noted that as long as such a function is not impaired, $R^2$ attached to the heterocyclic ring in Formula (I), (II) or (III) may be a hydrogen atom, an amino group, a hydroxyl group, a halogen atom, a $R^3$-oxy group, a $R^3$-amino group, or any other heteroatom (wherein $R^3$ is as defined above).

With respect to reaction conditions, for example, a nucleic acid carrying the compound of Formula (I) (about 25 μM) and DNA encoding its complementary sequence (about 25 μM) may be dissolved in a buffer (pH 7) containing 0.05 M MES and 0.1 M NaCl and reacted at room temperature. The progress of the reaction may be monitored by HPLC (ODS column, acetonitrile-0.1 M TEAA=10%-40% linear gradient/20 minutes).

The compound of Formula (I), (II) or (III) according to the present invention can recognize and bind to a specific base in a gene depending on the type of base. Moreover, an oligonucleic acid which is prepared from Compound (I), (II) or (III) and contains the compound as a constituent member may be hybridized with a single-stranded nucleic acid containing such a base to form a duplex.

Hybridization may be performed under stringent conditions. Stringent conditions mean, for example, a salt (sodium) concentration of 50 to 900 mM and a temperature of 10° C. to 50° C., preferably a salt (sodium) concentration of 50 to 150 mM and a temperature of 25° C.

In the present invention, there is no particular limitation on the type of base targeted by the nitrosyl group transfer reaction, and the target base may be either a purine base (adenine, guanine) or a pyrimidine base (cytosine, thymine). For example, as shown in the Example section below, in the case of using a purine base of Formula (I) (e.g., guanine) as a base structure, Compound (I) recognizes its corresponding cytosine base and is useful in achieving the nitrosyl group transfer reaction in a manner specific to a nucleic acid containing cytosine bases. It should be noted that the term "corresponding" means being complementary to the respective bases. Thus, a base corresponding to guanine is cytosine, by way of example.

The same also applies to other bases for hydrogen bond formation. In the case of using a pyrimidine base (cytosine, thymine) shown in Formula (II) or (III), the reaction is also possible for its corresponding base (G and A, respectively).

Figure 2:
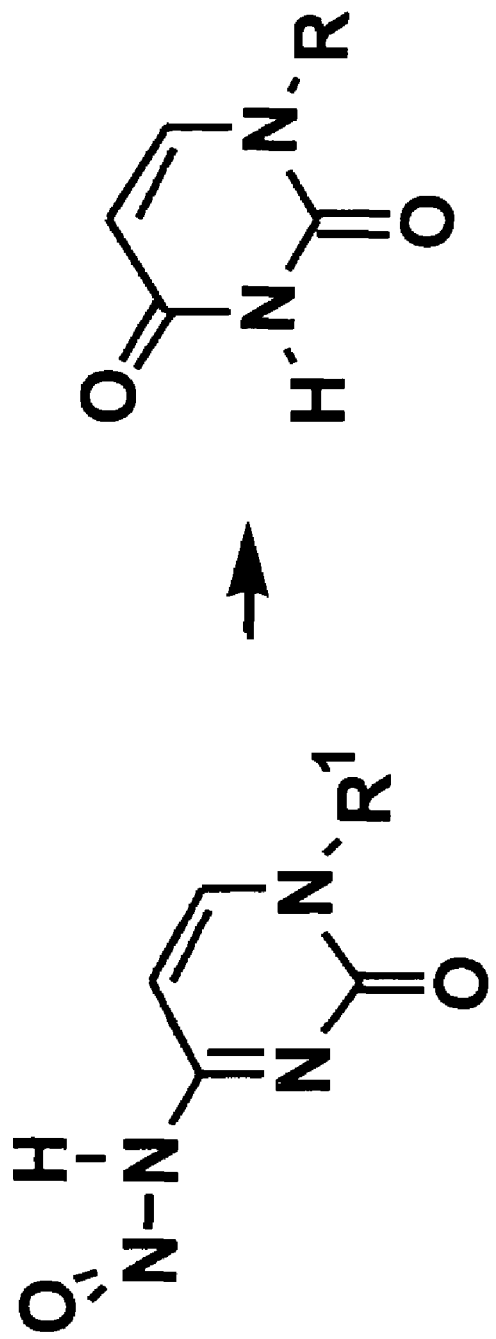
FIG. 2 shows hydrolysis reaction of the N-nitroso form into a carbonyl group.

The reaction is achieved in a hydrogen-bonded complex, as shown in FIG. 1. In addition, it is reported that N-nitrosocytosine is hydrolyzed into uracil (see, e.g., R. Glazer, R. Sundeep, M. Lewis, M.-S. Son, S. Meyer, J. Amer. Chem. Soc., 121, 6108 (1999)). Thus, in the present invention, cytidine can be converted into deoxyuridine in a sequence-specific manner (FIG. 2). This means that cytosine in an oligonucleic acid is mutated to uracil. In this case, the conversion reaction is performed under acidic conditions. Acidic conditions may be achieved by supplementing a reaction solution such as an aqueous solution or an organic buffer solution with, e.g., hydrochloric acid, acetic acid, sulfuric acid or phosphoric acid to adjust the pH to 2 to 6, preferably 4 to 5. Moreover, it is also possible to use various organic acids for pH adjustment. The reaction temperature ranges from 10° C. to 30° C., preferably 15° C. to 25° C., while the reaction time ranges from 10 to 40 hours, preferably 20 to 30 hours.

The compound of the present invention can be used as a compound for so-called drug delivery, which delivers NO active species to a specific site via sequence-specific nitrosyl group transfer reaction.

5. Mutagenic Agents or Mutagenesis Kits for Nucleotide Sequences

The compound or oligonucleic acid of the present invention can be used as a mutagenic agent or mutagenesis kit for nucleotide sequences. The mutagenic agent or mutagenesis kit of the present invention comprises at least one, possibly all, of the compounds or oligonucleic acids of the present invention. The term "nucleotide sequence" is intended to mean the nucleotide sequence of a nucleic acid such as DNA, cDNA, RNA or mRNA, regardless of whether it is derived from an organism or artificially synthesized. A nucleic acid for use as a template may be collected from, e.g., bacteria, yeast, animal cells, plant cells, insect cells or mammals by known procedures; any material having a nucleic acid (e.g., genome, plasmid) may be used for this purpose.

The oligonucleic acid is synthesized such that the compound of the present invention is located at the same position as that of a base to be mutated in the nucleotide sequence of the above template nucleic acid, i.e., such that the oligonucleic acid hybridizes to the nucleotide sequence serving as a template. After completion of the synthesis, the oligonucleic acid thus obtained may be hybridized with the template nucleic acid of interest to effect the above nitrosyl transfer reaction, and then treated under the acidic conditions mentioned above.

The kit of the present invention may comprise, in addition to the compound(s) of the present invention, a hybridization solution, a washing buffer, a fluorescent reagent, etc.

EXAMPLES

The present invention will be further illustrated by way of the following Examples, which are not intended to limit the scope of the invention.

Example 1

Synthesis of thionucleoside-S-nitrosyl derivative

Figure 4:
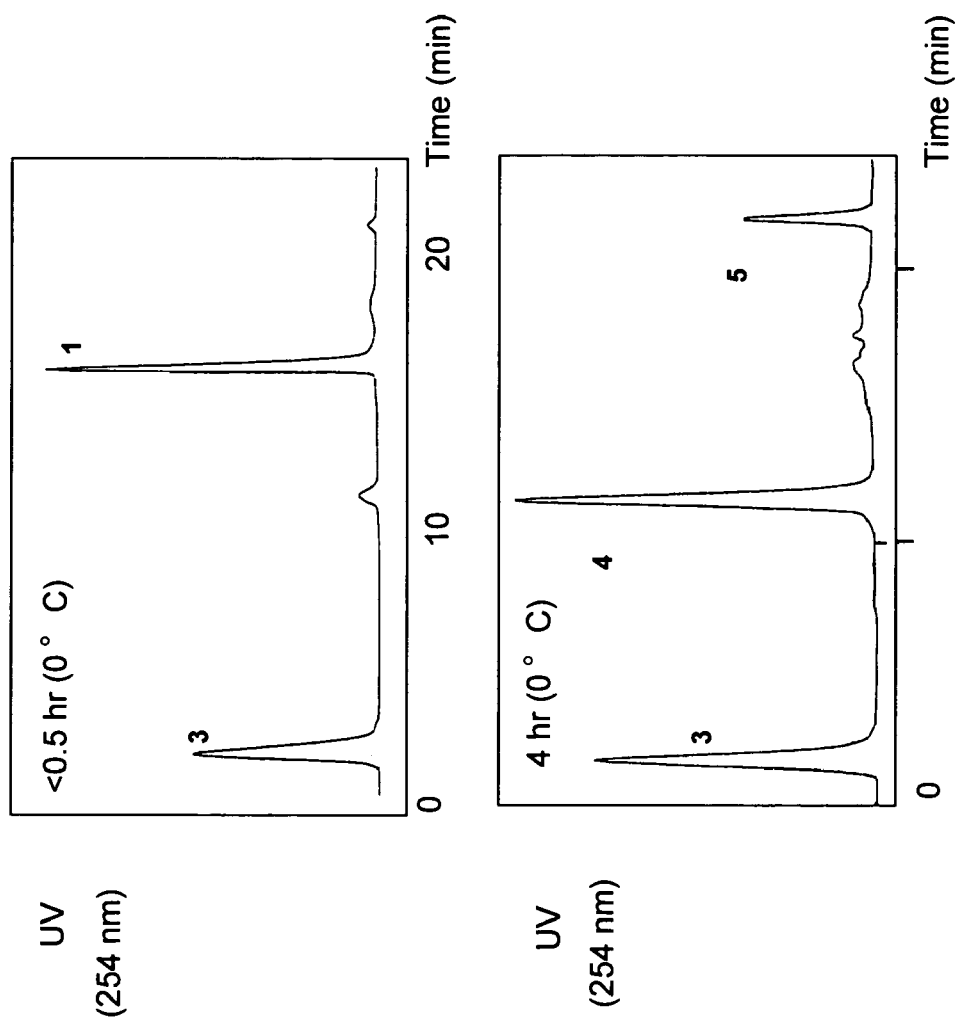
FIG. 4 shows the results of HPLC analysis for the nucleoside derivative of the present invention.

2'-Deoxy-6-thioguanosine (as a t-butyldimethylsilyl derivative) synthesized in a known manner (M. Kadokura, T. Wada, K. Seio, and M. Sekine J. Org. Chem., 65, 5104-5113 (2000)) (0.25 µmol), SNAP (2, S-nitroso-N-acetylpenicillamine) (0.25 µmol) and triethylamine (0.28 µmol) were dissolved in methanol (500 µl) and stirred at 0° C. The reaction solution was directly injected into HPLC-MS to measure ESI-MS (FIG. 4). HPLC conditions are as follows.

Column: Symmetry C18 2×50 mm

Column temperature: 25° C.

Mobile phase: A=$H_2O$, B=MeOH, % B=60-100%/5 min then 100% 20 min

Flow rate: 0.2 mL/min

UV: 254 nm

The HPLC eluate was separated by a splitter, about 1/40 (about 5 µL) of which was then introduced into a mass spectrometer. Mass spectrometry was performed in positive mode ESI-TOF. MS conditions (Applied biosystem Mariner System 5299) were set as follows: Spray Tip Potential, 4006, Nozzle potential 300, Nozzle temperature 140.

The results of mass spectrometry are shown below.

$t_R$ 1.1 min, MS m/z $(M+H)^+$ found 541.1705, calcld 541.2443 for 3 ($C_{22}H_{40}N_6S_1O_4Si_2$), $t_R$ 7.8 min, MS m/z $(M+H)^+$ found 701.4343, calcld 701.3001 for 4 (CHNSOSi), $t_R$ 15.0 min, MS m/z $(M+H)^+$ found 1021.4972, calcld 1021.4854 for 5 ($C_{44}H_{80}N_{10}S_2O_6Si_4$).

Figure 3:
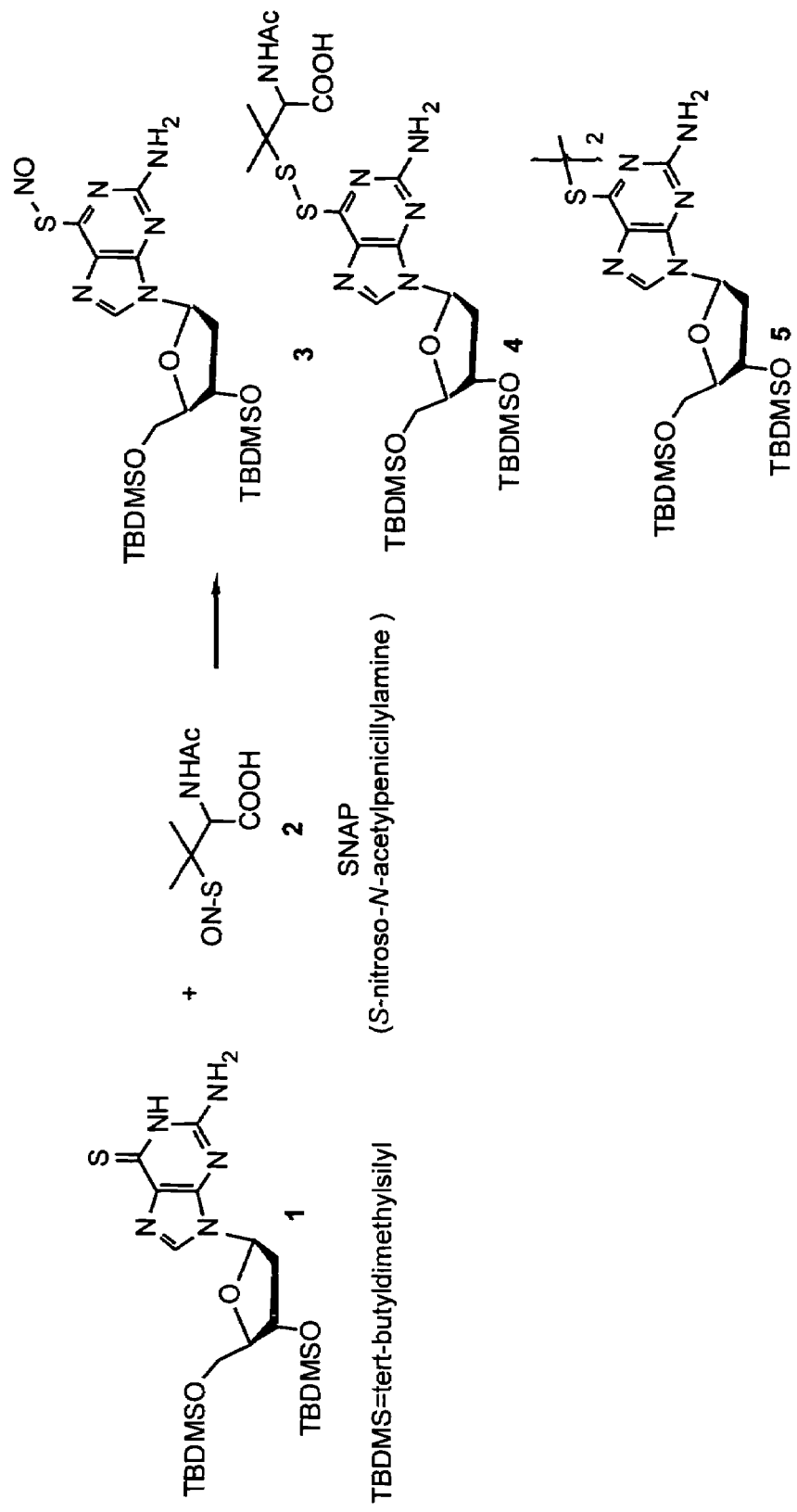
FIG. 3 shows a synthesis process for the nucleoside derivative of the present invention.

The time course observation shown in FIG. 4 demonstrated that the compound shown in FIG. 3, Scheme 3 or 4 was synthesized.

Example 2

Synthesis of Oligonucleic Acid

A 5'-O-dimethoxytrityl-3'-O-(2-cyanoethyl-N,N-diisopropylphosphoroamidite) form of S-(2-cyanoethyl)-2'-deoxy-6-thioguanosine, which had been synthesized in a known manner, was introduced into an oligonucleotide using a DNA synthesizer (model name: DNA/RNA Synthesizer, Applied Biosystems), followed by heating in 28% aqueous ammonia at 55° C. for 5 hours to obtain Oligonucleotide 6 (FIG. 5, Scheme 6; SEQ ID NO: 1). Oligonucleotide 6 (150 nmol) and SNAP (3 µmol) were dissolved in 300 µl carbonate buffer (pH 10.0) and allowed to stand at room temperature for 12 hours. After confirming the progress of the reaction by HPLC, a newly generated peak was isolated under the same HPLC conditions to thereby obtain Oligonucleotide 7 (SEQ ID NO: 2) shown in FIG. 5, Scheme 7. The yield was 31%, as measured by V absorbance at 260 nm. Moreover, when the molecular weight was determined by MALDI-TOF MASS, the measured value for molecular weight was found to be 4796.69, as compared to the theoretical value of 4797.76.

Example 3

$[NO^+]$ Generation Test by Digestion of Nucleotide 7

Into a fluorescence cell, a solution of Oligonucleotide 7 (FIG. 5) in MES buffer (0.05 M MES, 0.1 M NaCl, adjusted to pH 5 or pH 7, 1.5 mL, Oligonucleotide 7: 0.5 µM) was introduced and supplemented with DAF-2 (diaminofluoroscein, final concentration: 4 µM), followed by stirring at 25° C. The fluorescence spectrum of this reaction solution was measured over time (excitation wavelength: 488 nm, fluorescence wavelength: 500-600 nm). Simultaneously, 1 µl aliquots were also sampled over time from this solution and injected into HPLC to monitor the conversion of Oligonucleotide 7 into Oligonucleotide 6.

Figure 6:
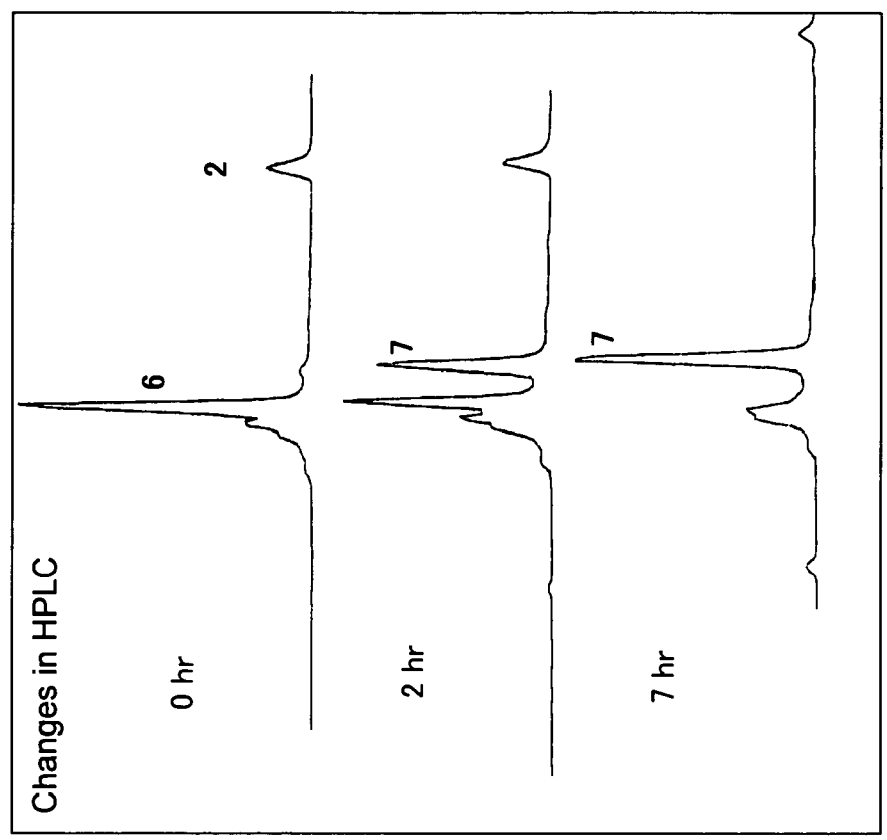
FIG. 6 shows the results of HPLC analysis for nitrosylated oligonucleic acid production.

Column: Nacalai tesque, COSMOSIL 5C18-MS (4.6×250 mm)
Mobile phase:
A: 0.1M TEAA Buffer, B: CH$_3$CN
B: 10% to 30%/20 min, 40%/30 min, linear gradient
Flow rate: 1.0 ml/min
UV-monitor: 260 nm The relative fluorescence intensity at 512 nm and percentage conversion into Oligonucleotide 6 were plotted on a graph (FIG. 6). At pH 5, the conversion of Oligonucleotide 7 into Oligonucleotide 6 tended to correlate well with the increasing curve of DAF-2 fluorescence intensity measured simultaneously (FIG. 7).

Figure 7:
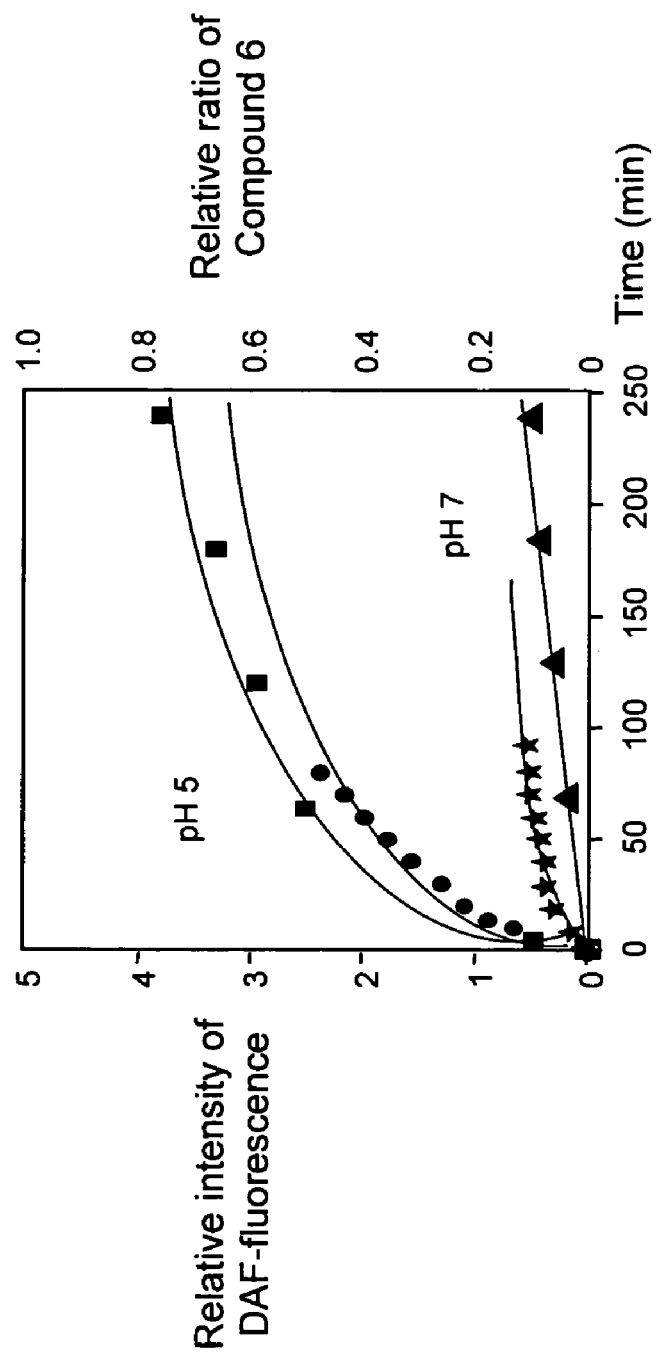
FIG. 7 shows increasing curves of fluorescence intensity of the nitrosylated oligonucleic acid DAF-2.

In FIG. 7, each symbol in the graph is as defined below.
● (solid circle): Fluorescence intensity of DAF-2 (diaminofluoresceine) in the reaction at pH 5 (which indicates the relative NO concentration).
★ (solid star): Fluorescence intensity of DAF-2 in the reaction at pH 7.
■ (solid square): Relative concentration of 6 in the reaction at pH 5 (which indicates regeneration of the thioguanosine form).
▲ (solid triangle): Relative concentration of 6 in the reaction at pH 7

This indicated that as Oligonucleotide 7 was converted into Oligonucleotide 6, chemical species equivalent to [NO$^+$] were released from Oligonucleotide 7 into the solution. In contrast, in the reaction solution at pH 7, there was little conversion of Oligonucleotide 7 into Oligonucleotide 6 and there was also little change in the fluorescence intensity of DAF-2 (FIG. 7). These results indicated that Oligonucleotide 7 was a stable precursor of chemical species equivalent to [NO$^+$].

Example 4

Reaction between Oligonucleotide 7 and its Complementary Oligonucleotide 8

Figure 8:
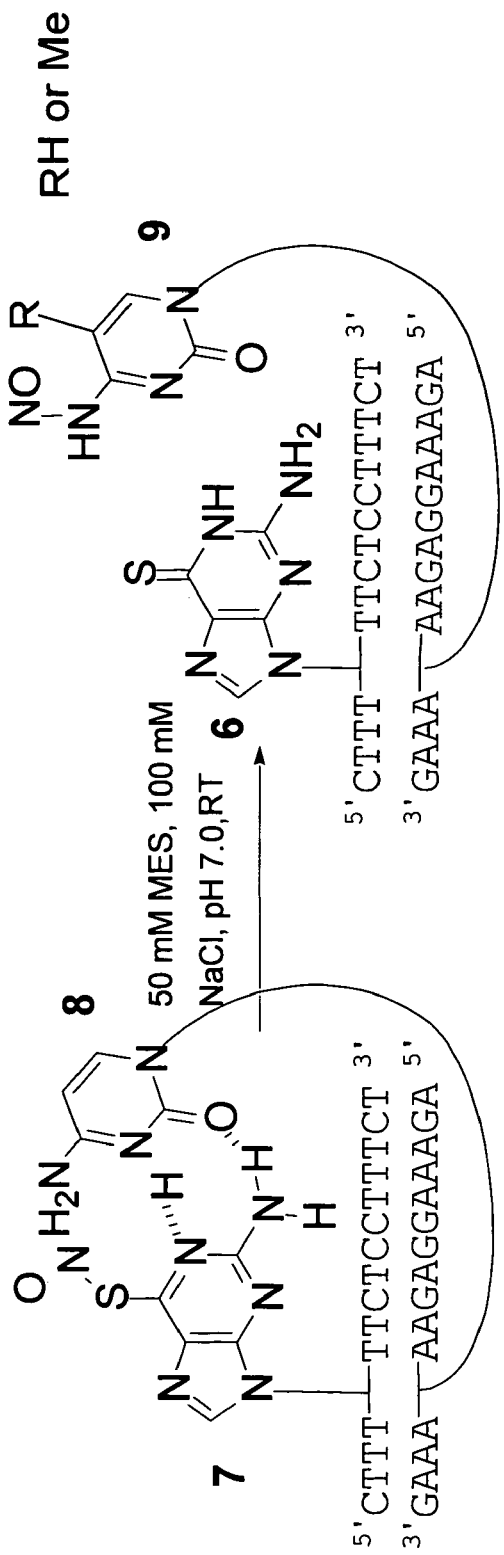
FIG. 8 shows the sequences of an oligonucleotide and its complementary strands, along with reaction between them.

As shown in FIG. 8, Oligonucleotide 7 (ODN(7),) and its complementary strand Oligonucleotide 8 (ODN(8)) were used for NO transfer reaction within a DNA duplex.

The reaction was performed in 50 mM MES buffer containing 100 mM NaCl at pH 7 at 25° C. using ODN(7) and ODN(8, 10-12) (10 µM each) or glutathione (1 mM).

```
ODN(6):      SEQ ID NO: 1
ODN(7):      SEQ ID NO: 2
ODN(8):      SEQ ID NO: 3
ODN(9):      SEQ ID NO: 4
ODN(10):     SEQ ID NO: 5
ODN(11):     SEQ ID NO: 6
ODN(12):     SEQ ID NO: 7
```

Figure 9:
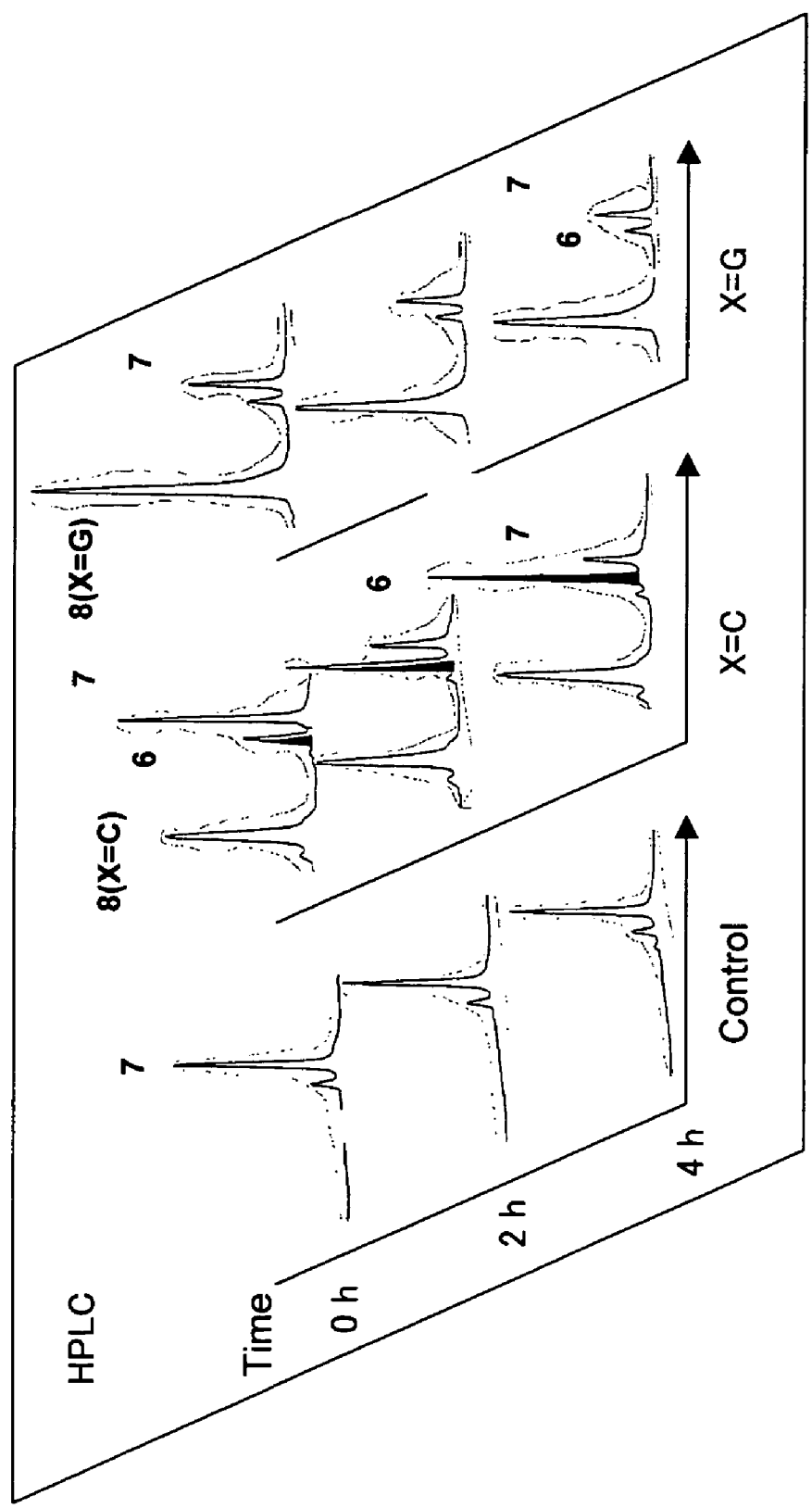
FIG. 9 shows the results of HPLC analysis for NO transfer reaction.
Figure 10:
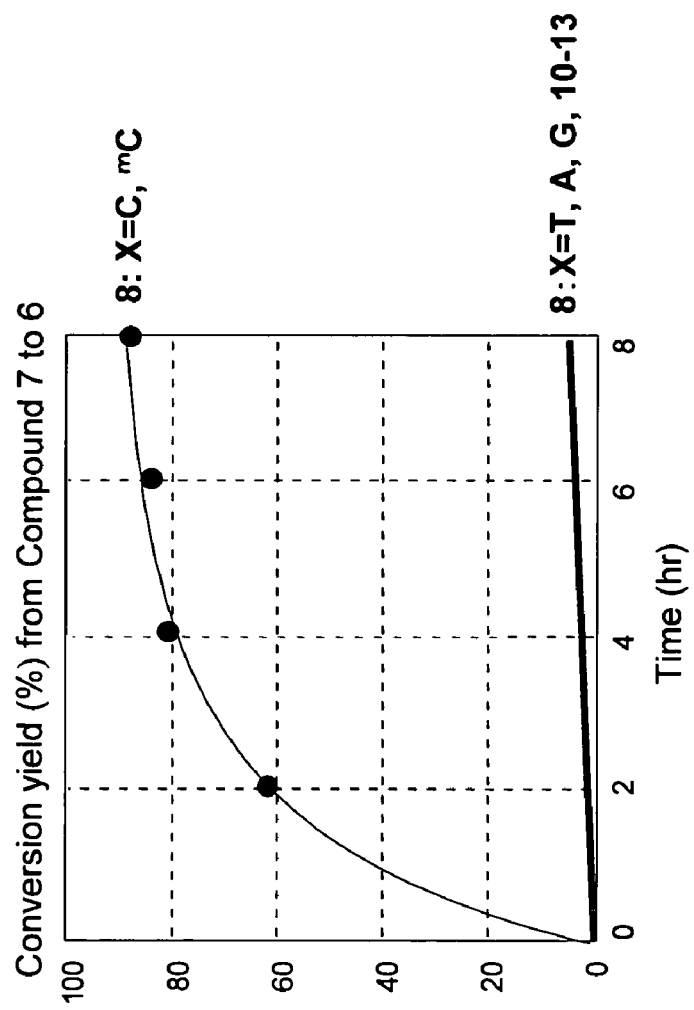
FIG. 10 shows the time course of NO transfer reaction using Oligonucleotide 7.

The reaction mixture was analyzed by HPLC. HPLC conditions are shown below.
ODS column, 1 mL/min
Mobile phase:
A: 0.1M TEAA Buffer, B: CH$_3$CN
B: 10% to 30%/20 min, 40%/30 min, linear gradient
Monitor: 260 nm The results obtained are shown in FIGS. 9 and 10. When ODN(7) was reacted with ODN(8) having dC (cytidine) or d$^m$C (5-methylcytidine), a rapid conversion reaction of ODN(7) occurred to give 6 (SEQ ID NO: 1). In contrast, the rate of the reaction with ODN(8) having dT, dA or dG was at background levels. Thus, ODN(7) was clearly shown to have a high selectivity toward dC and d$^m$C. In the case of ODN(10-12) having dC at a different site other than the target site, no transfer reaction occurred. This indicates that ODN(7) has a high site selectivity. Likewise, glutathione did not react with ODN(7) under conditions of physiological concentration (1 mM). These results indicate that the high selective reactivity of ODN(7) was due to a sufficient proximity effect between S—NO thioguanosine and its target dC or d$^m$C in the DNA duplex.

Example 5

Reaction between S—NO Oligonucleotide 7 or NO-Receiving Oligonucleotide 8 and DAF-2

Figure 11:
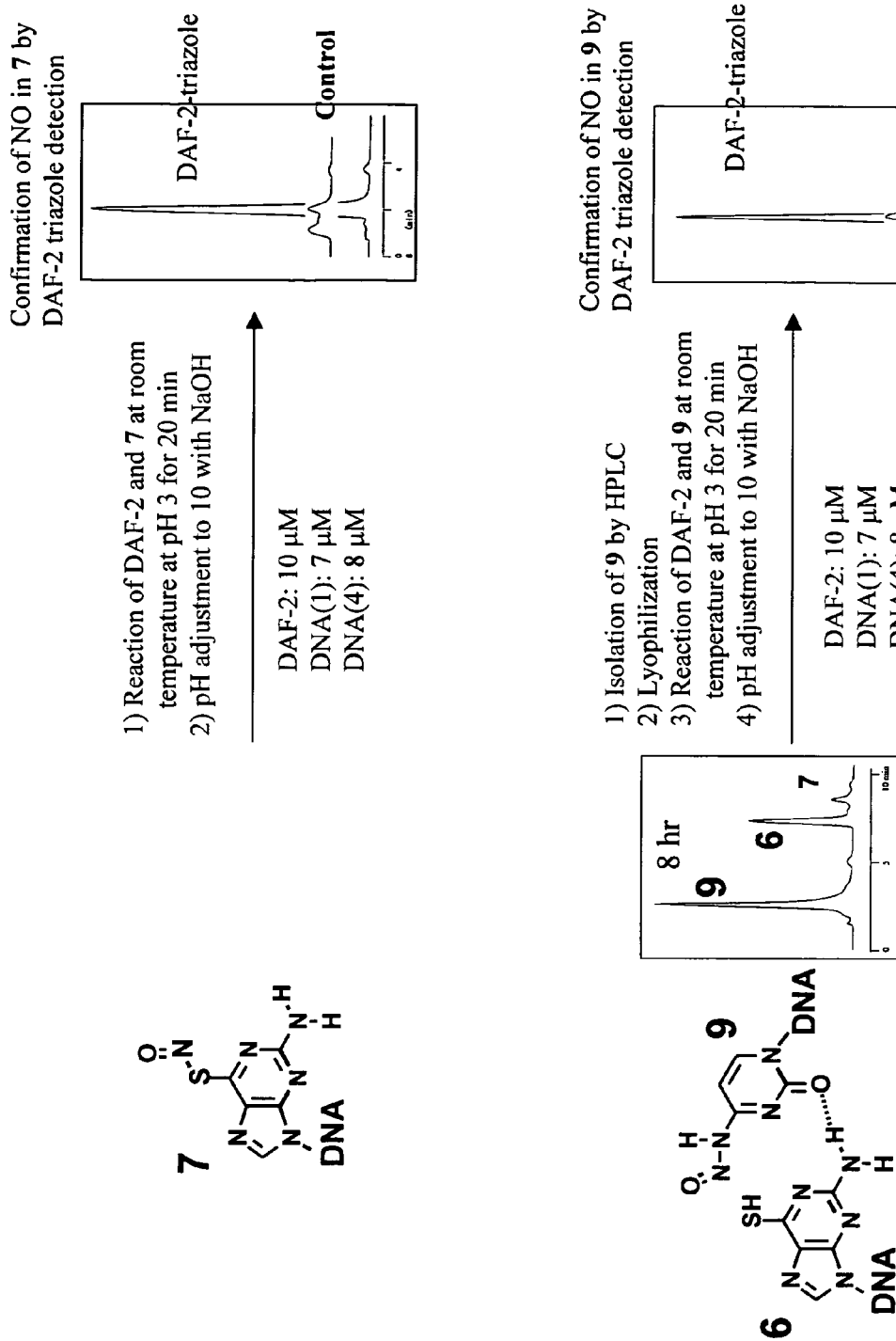
FIG. 11 shows HPLC analysis for reaction products between Oligonucleotide 7 or Oligonucleotide 9 and DAF-2. This analysis confirms the presence of NO.

The reaction solution of Oligonucleotide 7 and Oligonucleotide 8 (X=C) was analyzed in the presence of an NO-detecting fluorescent dye DAF-2 to monitor changes in its fluorescence spectrum, indicating that there was little change in the fluorescence intensity. This confirmed that chemical species equivalent to [NO$^+$], which had been released from Oligonucleotide 7 during this reaction, were not released into the solution. The transfer of NO from Compound 2 to Compound 3 was confirmed using the same fluorescent reagent DAF-2 (FIG. 11). ODN(7) and DAF-2 were mixed and incubated at pH 3 at room temperature for 20 minutes, and the resulting mixture was alkalized with NaOH solution to pH 10 and then analyzed by HPLC. The presence of NO species was clearly demonstrated by detecting the peak of a triazole derivative of DAF-2. Likewise, DAF-2 was also mixed with ODN(9) (X=dC or d$^m$C) isolated from the reaction mixture at 8 hours after initiation of the transfer reaction, followed by detecting the peak of a DAF-2 triazole derivative in the same manner as mentioned above. As a result, there appeared a peak having almost the same intensity as obtained for ODN(7). These results clearly indicate that NO is transferred from ODN(7) to ODN(8) (X=dC, d$^m$C) with high efficiency and that NO-receiving ODN(9) is stable under isolation conditions.

Example 6

Figure 12:
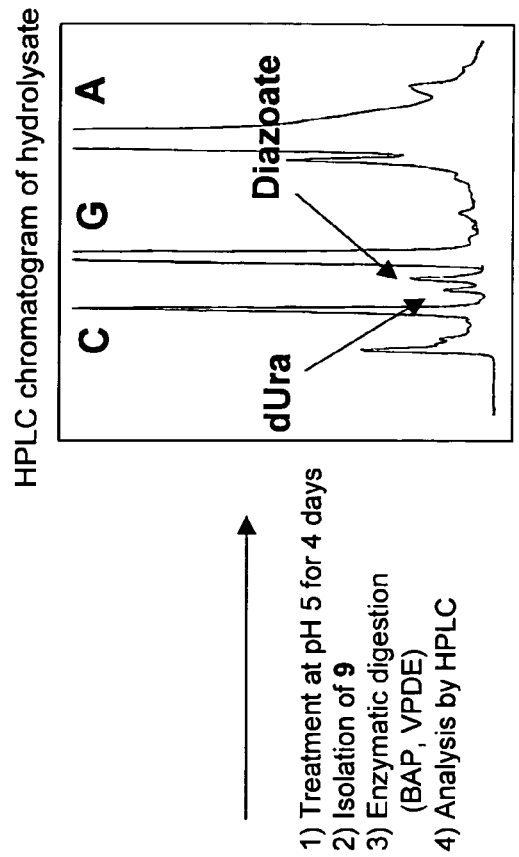
FIG. 12 shows HPLC analysis for an enzymatic hydrolysate of Oligonucleotide 9 generated from Oligonucleotide 8 as a result of NO transfer. This analysis demonstrates that cytidine was mutated to deoxyuridine and cytidine diazoate.
Figure 12:
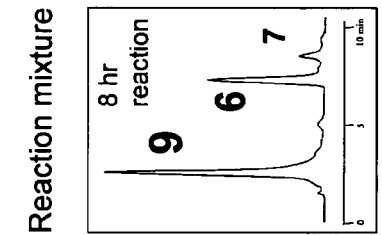
Figure 12:
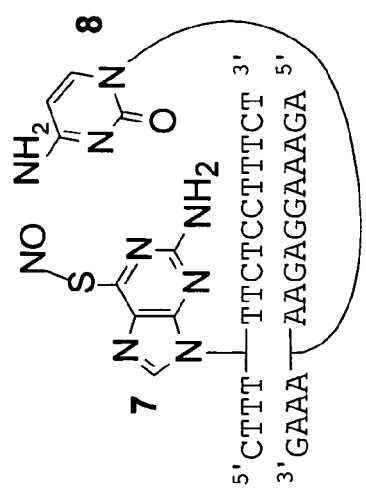
Figure 12:
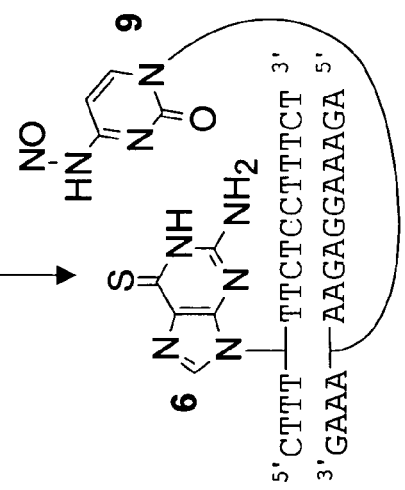

Acid Treatment and Enzymatic Hydrolysis on Complementary Oligonucleotide 9 (X=C) After Reaction As shown in FIG. 12, a solution containing Oligonucleotides 7 and 8 (about 20 µM each) in MES buffer (0.05 M MES, 0.1 M NaCl, pH 7) was reacted at 25° C. for 8 hours. Subsequently, the solution was adjusted to pH 5 and allowed to stand at the same temperature for an additional 30 hours. Oligonucleotide 9 was isolated from this reaction mixture by HPLC and lyophilized.

HPLC conditions are as follows.
Column: Nacalai tesque, COSMOSIL 5C18-MS (4.6×250 mm)
Mobile phase: A=0.1 M TEAA buffer, B=CH$_3$CN, 10% to 30%/20 min, 40%/30 min, linear gradient
Flow rate: 1.0 ml/min
UV-monitor: 260 nm The isolated Oligonucleotide 9 was enzymatically hydrolyzed and the resulting nucleosides were analyzed by HPLC. Conditions for enzymatic hydrolysis and HPLC are as follows.

Enzymatic Hydrolysis Reaction
  BAP: bacteria alkaline phosphatase
  VPDE: venom phosphodiesterase
  Buffer: 0.1 M Tris, 0.1 M NaCl, 14 mM $MgCl_2$, 37° C., pH 7

HPLC Conditions
  Column: Nacalai tesque, COSMOSIL 5C18-MS (4.6×250 mm)
  Mobile phase: A=0.1 M TEAA buffer, B=$CH_3CN$, 10% to 30%/20 min, 40%/30 min, linear gradient
  Flow rate: 1.0 ml/min
  UV-monitor: 260 nm The results of enzymatic hydrolysate analysis indicated that in addition to C, G and A contained in Oligonucleotide 9,2'-deoxyuridine and cytidine diazoate were obtained in 8% and 14%, respectively (FIG. 12). It was therefore demonstrated that the 12th base C (5th base from the 3'-end) in Oligonucleotide 9 was converted into its corresponding base (X=dU) in Oligonucleotide 8 (i.e., mutation from cytosine to uracil).

Example 7

Figure 13:
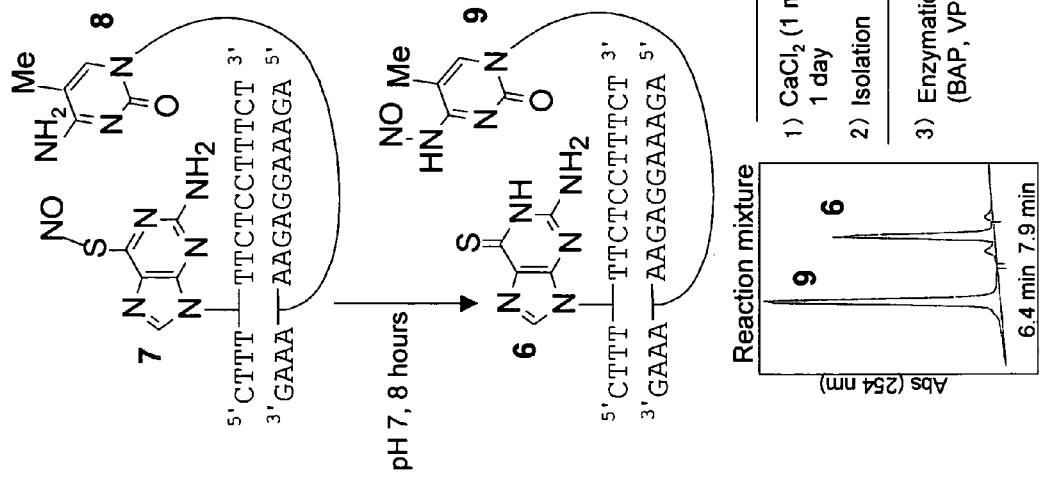
FIG. 13 shows HPLC analysis for an enzymatic hydrolysate of Oligonucleotide 9 generated from Oligonucleotide 8 as a result of NO transfer. This analysis demonstrates that 5-methylcytidine was mutated to thymidine and 5-methylcytidine diazoate.

Acid Treatment and Enzymatic Hydrolysis on Complementary Oligonucleotide 9 (X=5-methyl C) After Reaction As shown in FIG. 13, a solution containing Oligonucleotides 7 and 8 (about 20 μM each) in MES buffer (0.05 M MES, 0.1 M NaCl, pH 7) was reacted at 25° C. for 8 hours. Subsequently, the solution was adjusted to pH 5, supplemented with $CaCl_2$, $ZnCl_2$ or $MgCl_2$ (5 mM) and allowed to stand at the same temperature for an additional 1 day. Oligonucleotide 9 was isolated from this reaction mixture by HPLC and lyophilized. This product was hydrolyzed with BAP and BPDE, and then applied to HPLC. Conditions for enzymatic reaction and HPLC are as follows.

Enzymatic Hydrolysis Reaction
  BAP: bacteria alkaline phosphatase
  VPDE: venom phosphodiesterase
  Buffer: 0.1 M Tris, 0.1 M NaCl, 14 mM $MgCl_2$, 37° C., pH 7
  ODS column, 4.6×200 mm,
  Mobile phase: A=50 mM $HCOONH_4$, B=$CH_3CN$, 2% to 20%/50 min, linear gradient
  Flow rate: 1.0 ml/min
  UV-monitor: 254 nm A control experiment was performed in the same manner as mentioned above using ODN(1) and its target ODN(3).

The results obtained are shown in FIG. 13. FIG. 13 clearly confirms the generation of dT. Moreover, the peak marked with an asterisk (*) shows the same retention time as $d^mC$-diazoate synthesized as previously reported (Suzuki, T. et al., Bioorg. Med. Chem. Lett. 2002, 10, 1063-1067). It is noteworthy that the rate of conversion from $d^mC$ to dT is as high as 42%, along with conversion into $d^mC$-diazoate (13%) (FIG. 13).

Since there is no large peak indicative of a deaminated product of dG or dA, this NO transfer reaction is found to have a high base selectivity. These results indicate that NO is transferred to the amino group of dC or $d^mC$. Likewise, as mentioned in the section of the DAF-2 experiment, N—NO species in ODN(9) are stable. Thus, the reason that dC or $d^mC$ is observed by the enzymatic reaction is expected at this stage to be because the N—NO species return to dC or $d^mC$ during the enzymatic hydrolysis reaction.

In view of the foregoing, the efficiency of NO transfer and subsequent deamination is extremely high when compared to conventional techniques using NO gas or other nitrosylating agents. The present invention is therefore useful in understanding the role of NO in DNA damage. Moreover, the novel NO delivery method of the present invention can be adapted to achieve site-specific mutagenesis selectively during the translation or polymerization step.

INDUSTRIAL APPLICABILITY

The present invention provides a thionucleoside-S-nitrosyl derivative. The derivative of the present invention is useful as a tool for point mutagenesis of a target base because the derivative can transfer its nitrosyl group in a sequence-specific and base-specific manner to cause base replacement in its complementary strand.

Sequence Listing Free Text

SEQ ID NO: 1: Synthetic nucleotide
SEQ ID NO: 1: n represents a thionucleotide derivative of a, g, c or t (Location: 5)
SEQ ID NO: 2: Synthetic nucleotide
SEQ ID NO: 2: n represents a thionucleotide nitrosyl derivative of a, g, c or t (Location: 5)
SEQ ID NO: 3: Synthetic nucleotide
SEQ ID NO: 3: n represents a, g, c or t (Location: 12).
SEQ ID NO: 4: Synthetic nucleotide
SEQ ID NO: 4: n represents a nitrosyl derivative of a, g, c or t (Location: 12).
SEQ ID NO: 5: Synthetic nucleotide
SEQ ID NO: 6: Synthetic nucleotide
SEQ ID NO: 7: Synthetic nucleotide

The invention claimed is:

1. A thionucleoside-S-nitrosyl derivative of the following Formula (I) or a salt thereof:

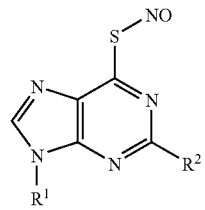

(I)

wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group, wherein $R^3$ represents an optionally substituted $C_{1-15}$ alkyl group or an optionally substituted $C_{1-15}$ acyl group.

2. A method for preparing a thionucleoside-S-nitrosyl derivative, which comprises reacting a thionucleoside of the following Formula (IV):

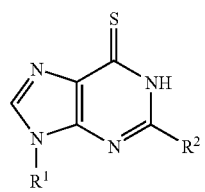

(IV)

wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group, wherein $R^3$ represents an optionally substituted $C_{1-15}$ alkyl group or an optionally substituted $C_{1-15}$ acyl group with a nitrosyl compound.

3. An oligonucleic acid comprising the derivative according to claim 1 or a salt thereof.

4. The oligonucleic acid according to claim 3, which has a length of at least 12 bases.

5. A method for transferring a nitrosyl group, which comprises reacting the oligonucleic acid according to claim 3 with its complementary strand to transfer the nitrosyl group contained in the oligonucleic acid to a corresponding base in its complementary strand.

6. A method for mutagenesis of a nucleotide sequence, which comprises reacting the oligonucleic acid according to claim 3 with its complementary strand, and treating the resulting reaction product under acidic conditions.

7. The method according to claim 6, wherein the nucleotide sequence is a nucleotide sequence corresponding to the derivative in the oligonucleic acid.

8. The method according to claim 6, wherein the mutagenesis generates a mutation to uracil.

9. A mutagenic agent for a nucleotide sequence, which comprises at least one member selected from the group consisting of a thionucleoside-S-nitrosyl derivative of the following Formula (I) or a salt thereof:

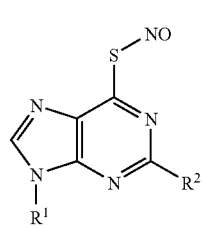

(I)

wherein $R^1$ represents ribose, 2-deoxyribose or a derivative of either and $R^2$ represents a hydrogen atom, an amino group, a hydroxyl group, a halogen atom, a $R^3$-oxy group or a $R^3$-amino group wherein $R^3$ represents an optionally substituted $C_{1-15}$ alkyl group or an optionally substituted $C_{1-15}$ acyl group;

a thionucleoside-S-nitrosyl derivative of the following Formula (II) or a salt thereof:

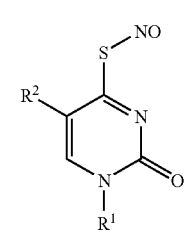

(II)

wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group wherein $R^3$ represents an optionally substituted $C_{1-15}$ alkyl group or an optionally substituted $C_{1-15}$ acyl group;

a thionucleoside-S-nitrosyl derivative of the following Formula (III) or a salt thereof:

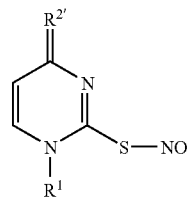

(III)

wherein $R^1$ represents ribose, 2-deoxyribose or a derivative of either, and $R^{2'}$ represents an oxygen atom, a sulfur atom or an imino group;

an oligonucleic acids comprising the derivative according to formula I; an oligonucleic acid comprising the derivative according to formula II; and an oligonucleic acid comprising the derivative according to formula III.

10. A mutagenesis kit for a nucleotide sequence, which comprises at least one member selected from the group consisting of a thionucleoside-S-nitrosyl derivative of the following Formula (I) or a salt thereof:

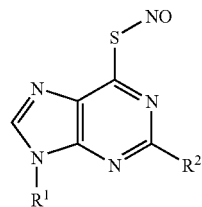

(I)

wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group wherein $R^3$ represents an optionally substituted $C_{1-15}$ alkyl group or an optionally substituted $C_{1-15}$ acyl group;

a thionucleoside-S-nitrosyl derivative of the following Formula (II) or a salt thereof:

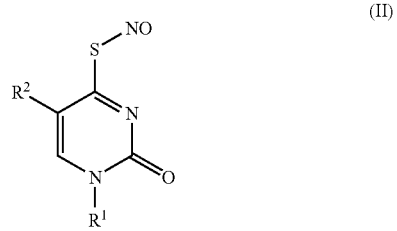

(II)

wherein $R^1$ represents ribose, 2-deoxyribose or a derivative of either, and $R^2$ represents a hydrogen atom, an amino group, a hydroxyl group, a halogen atom, a $R^3$-oxy group or a $R^3$-amino group wherein $R^3$ represents an optionally substituted $C_{1-15}$ alkyl group or an optionally substituted $C_{1-15}$ acyl group;

a thionucleoside-S-nitrosyl derivative of the following Formula (III) or a salt thereof:

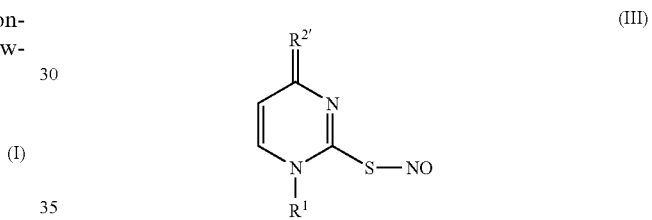

(III)

wherein $R^1$ represents ribose, 2-deoxyribose or a derivative of either, and $R^{2'}$ represents an oxygen atom, a sulfur atom or an imino group);

an oligonucleic acid comprising the derivative according to formula I; an oligonucleic acid comprising the derivative according to formula II; and an oligonucleic acid comprising the derivative according to formula III.

* * * * *

SEQUENCE LISTING

```
<160> NUMBER OF SEQ ID NOS: 7

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide
<220> FEATURE:
<221> NAME/KEY: modified base
<222> LOCATION: 5
```

-continued

```
<223> OTHER INFORMATION: n represents thionucleotide derivative of a,
      g, c or t

<400> SEQUENCE: 1
ctttnttctc ctttct                                                    16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide
<220> FEATURE:
<221> NAME/KEY: modified base
<222> LOCATION: 5
<223> OTHER INFORMATION: n represents thionucleotide nitrosyl derivative
      of a, g, c or t

<400> SEQUENCE: 2
ctttnttctc ctttct                                                    16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide
<220> FEATURE:
<221> NAME/KEY: modified base
<222> LOCATION: 12
<223> OTHER INFORMATION: n represents a, g, c or

<400> SEQUENCE: 3
agaaaggaga anaaag                                                    16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide
<220> FEATURE:
<221> NAME/KEY: modified base
<222> LOCATION: 12
<223> OTHER INFORMATION: n represents nitrosyl derivative of a, g, c or
      t

<400> SEQUENCE: 4
agaaaggaga anaaag                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide

<400> SEQUENCE: 5
agaaaggaga ctaaag                                                    16

<210> SEQ ID NO 6
<211> LENGTH: 16
<212> TYPE: DNA
<213> ORGANISM: Artificial Sequence
<220> FEATURE:
```

-continued

```
<223> OTHER INFORMATION: Description of Artificial Sequence: synthetic
      nucleotide

<400> SEQUENCE: 6
agaaaggagc ataaag                                                      16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: synthetic
      nucleotide

<400> SEQUENCE: 7
agaaaggaca ataaag                                                      16
```